United States Patent
Rosier

(10) Patent No.: US 8,957,237 B2
(45) Date of Patent: Feb. 17, 2015

(54) METHOD FOR THE DIRECT SYNTHESIS OF ALKYLHALOGENOSILANES

(71) Applicant: Bluestar Silicones France, Lyons (FR)

(72) Inventor: Cécile Rosier, Satin Laurent d'Agny (FR)

(73) Assignee: Bluestar Silicones France SAS, Lyons (FR)

( * ) Notice: Subject to any disclaimer, the term of this patent is extended or adjusted under 35 U.S.C. 154(b) by 0 days.

(21) Appl. No.: 14/368,179

(22) PCT Filed: Dec. 18, 2012

(86) PCT No.: PCT/FR2012/000526
§ 371 (c)(1),
(2) Date: Jun. 23, 2014

(87) PCT Pub. No.: WO2013/093234
PCT Pub. Date: Jun. 27, 2013

(65) Prior Publication Data
US 2014/0364640 A1 Dec. 11, 2014

(30) Foreign Application Priority Data

Dec. 19, 2011 (FR) ..................................... 11 03922

(51) Int. Cl.
*C07F 7/16* (2006.01)
*B01J 23/80* (2006.01)
*B01J 27/10* (2006.01)
*B01J 23/835* (2006.01)

(52) U.S. Cl.
CPC . *C07F 7/16* (2013.01); *B01J 27/10* (2013.01); *B01J 23/835* (2013.01); *B01J 23/80* (2013.01)
USPC ............................................ 556/472; 502/226

(58) Field of Classification Search
CPC ............. C07F 7/16; B01J 23/30; B01J 23/835
USPC ............................................ 556/472; 502/226
See application file for complete search history.

(56) References Cited

U.S. PATENT DOCUMENTS

| 5,059,343 | A | | 10/1991 | Halm et al. | |
| 5,986,123 | A | * | 11/1999 | Nakayama et al. | 556/472 |
| 6,025,513 | A | * | 2/2000 | Nakanishi et al. | 556/472 |
| 6,258,970 | B1 | | 7/2001 | Ward, III et al. | |
| 7,179,933 | B2 | * | 2/2007 | Inukai et al. | 556/472 |
| 8,416,297 | B2 | * | 4/2013 | Finn et al. | 348/143 |
| 2002/0183536 | A1 | * | 12/2002 | Aramata et al. | 556/472 |
| 2003/0171606 | A1 | * | 9/2003 | Margaria | 556/472 |

FOREIGN PATENT DOCUMENTS

FR 2848124 A1 6/2004
FR 2848211 A1 6/2004

OTHER PUBLICATIONS

International Search Report dated Apr. 16, 2013 corresponding to International Patent Application No. PCT/FR2012/000526, 4 pages (including English translation).

* cited by examiner

Primary Examiner — Porfirio Nazario Gonzalez
(74) Attorney, Agent, or Firm — Dentons US LLP

(57) ABSTRACT

An improved industrial method for the direct synthesis of alkylhalogenosilanes is described. Specifically, a method is described for preparing alkylhalogenosilanes by reacting, in a fluidized bed reactor, and alkyl halogenide, preferably $CH_3Cl$, with a solid body, which is referred to as a contact body and which includes powdered silicon and a catalytic system including at least one copper catalyst and β1 and β2 promoter activities.

13 Claims, No Drawings

METHOD FOR THE DIRECT SYNTHESIS OF ALKYLHALOGENOSILANES

CROSS-REFERENCE TO PRIOR APPLICATIONS

This application is a National Stage of PCT/FR2012/000526, filed Dec. 18, 2012, and designating the United States (published in English on Jun. 27, 2013, as WO 2013/093234 A1), which claims priority under 35 U.S.C. §119 to French Patent Application No. 11 03922, filed Dec. 19, 2011, each hereby expressly incorporated by reference in its entirety and each assigned to the assignee hereof.

The present invention pertains to improvements relating to the industrial process implemented for the direct synthesis of alkylhalosilanes.

The industrial process for manufacture of alkylhalosilanes such as, for example, dimethyldichlorosilane, referred to subsequently as DMDCS, is a well known process which is described in particular in the United States of America patent U.S. Pat. No. 2,380,995, and also in the work by Walter Noll, Chemistry and Technology of Silicones, 1968, published by Académie Press Inc., London, pages 26-41.

According to this "direct synthesis" or "Rochow synthesis" process, the alkylhalosilanes, DMDCS for example, are manufactured directly by reaction of methyl chloride with a solid contact material formed of silicon and of a catalyst comprising copper, in accordance with the following reaction:

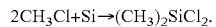

$$2CH_3Cl+Si \rightarrow (CH_3)_2SiCl_2.$$

In actual fact, other coproducts are formed during the direct synthesis, such as those referred to hereinafter: other alkylhalosilanes such as methyltrichlorosilane $CH_3SiCl_3$, subsequently referred to as MTCS, and trimethyl-chlorosilane $(CH_3)_3SiCl$, subsequently referred to as TMCS; halogenated alkylhydrosilanes such as, for example, methyl-hydrodichlorosilane $(CH_3)HSiCl_2$, subsequently referred to as MHDCS; and heavy products, these being polysilanes, and more particularly disilanes such as, for example, trimethyltrichlorodisilane $(CH_3)_3Si_2Cl_3$, dimethyltetra-chlorodisilane $(CH_3)_2Si_2Cl_4$, and tetramethyldichlorodisilane $(CH_3)_4Si_2Cl_2$.

Among all of the products obtained by direct synthesis, the dialkyldihalosilane, and for example the DMDCS, is the main product, in other words the product obtained in majority amount. This product is highly sought after because, after hydrolysis and polymerization, it yields oils and gums which are base products in the silicones field.

The use is known of copper, employed in the form of metallic copper or in the form of chemical compounds based on copper, as catalyst for the direct synthesis reaction. Also known, for the purpose of enhancing the performance characteristics of the direct synthesis, is to admix the copper with a promoter combination comprising one or more promoter additives; these additives may be as follows: zinc or a zinc halide (U.S. Pat. No. 2,464,033), aluminum (U.S. Pat. Nos. 2,403,370 and 2,427,605), tin, manganese, nickel, and silver (British patent GB-A-1 207 466), cobalt (British patent GB-A-907 161), potassium chloride, arsenic, or an arsenic compound (U.S. Pat. No. 4,762,940).

The direct synthesis process may be implemented in various types of industrial reactors, such as, for example, an agitated bed reactor like that described in United States of America patent U.S. Pat. No. 2,449,821 or a fluidized bed reactor like that described in United States of America patent U.S. Pat. No. 2,389,931. Its implementation in a fluidized bed reactor is the most widespread form. In this process, the reactor is fed continuously with alkyl halide, and for example with methyl chloride, and is fed continuously or semicontinuously with silicon to replace that consumed in the production of the alkylhalosilanes. It is known that as the reaction progresses, the selectivity for target product (the dialkyldihalosilane, and for example the DMDCS) and the activity of the reaction (which may be measured, for example, as grams of dialkyldihalosilanes formed per kg of silicon per hour) reduce in line with the accumulation within the reaction material of impurities originating from the starting silicon that do not react with the methyl chloride. This accumulation of impurities, and particularly aluminum, gives rise to a deterioration in the selectivity and activity of the reaction, and promotes deposits of carbon (or coke) in the reactor. Research is continuing in this field, since the industrial conditions in which the direct synthesis process is implemented give rise, in a manner known per se [cf. Journal of Catalysis 161, 861-866 (1996)], to side reactions of cracking of the starting alkyl halide, these side reactions leading to the formation of coke and hydrocarbons. This coke formation is the cause in particular of the fouling of the direct synthesis reactor within which the coke deposits are laid down. These coke deposits are very hard and difficult to clean as they may have a thickness of several dozen centimeters. This unwelcome fouling necessitates periodic cleaning operations, thereby reducing the production capacity of the plant accordingly. Moreover, the deposition of carbon, which occurs on the surface of the grains of silicon as well, is greatly suspected to be a factor in the deterioration in the activity and selectivity of the reaction.

When the selectivity and activity of the reaction are no longer economically acceptable, operation is halted. The reaction material present in the reactor, formed of silicon, catalysts, and impurities (and also called spent mass), is discharged, the reactor is cleaned, and another industrial operation is started with new silicon. The fewer the deposits of carbon in the reactor, the easier the cleaning step.

Patent application WO 2011/046663 describes a process for manufacturing alkylhalosilanes which extends the duration for which the selectivity for dialkyldihalosilane and the rate of conversion of the silicon are economically viable, and also reduces carbon deposits. In that application, the use is described of a silicon with a very low aluminum content (of between 0.001 and 0.10 weight %). That application says nothing about the problems and solutions linked to the need to maintain sufficient activity of the reaction material for industrial production of alky-halosilanes.

It is known, though, that the amount of aluminum in the silicon introduced into the reactor has a substantial effect on the cracking of the methyl chloride. Increases in the level of aluminum and in the degree to which the methyl chloride is cracked have the effect of promoting deposits of carbon in the reactor and on the surface of the silicon grains (LD Gasper-Calvin et al., Journal of Catalysis, 128 (1991) p. 468). It is also known, however, that the level of aluminum present in the silicon introduced into the reactor has a substantial effect on the activity of the reaction. Accordingly, the use of a silicon having a very low aluminum concentration results in a drop in activity of the reaction material ("The effect of low aluminum silicon on the direct process", JM Bablin et al., Silicon for the Chemical Industry VI (2002), p. 323).

There is therefore an interest in improving the process for preparing alkylhalosilanes in order to maintain for as long as possible a good level of selectivity for dialkyldihalosilane and a high activity of the reaction, while reducing the carbon deposits in the reactor and on the surface of the silicon grains.

One of the objectives of the present application is to provide a process for preparing alkylhalosilanes that combines:

a) high activity of the reaction,
b) high selectivity for dialkyldihalosilane, and
c) high lifetime of the catalytic material.

The present invention accordingly provides a process for preparing alkylhalosilanes by reacting an alkyl halide, preferably $CH_3Cl$, with a solid material, termed contact material, formed of silicon powder and a catalytic system comprising at least one copper-based catalyst and promoter additives β1 and β2 in a fluidized bed reactor, said process being characterized in that:

a) a first silicon Si1 is introduced, having an aluminum content of 0.10 to 0.18 weight %, a calcium content of less than 0.2 weight %, and a phosphorus content of less than 50 weight ppm, then b) a second silicon Si2 is introduced, alone or optionally in a mixture with Si1, having an aluminum content of 0.10 to 0.15 weight %, a calcium content of less than 0.2 weight %, and a phosphorus content of between 50 and 250 weight ppm.

It is understood that the silicon Si2 is different from the silicon Si1. They are always different at least in their phosphorus content.

The first silicon Si2 preferably has a phosphorus content of less than 40 weight ppm. Even more advantageously, the first silicon Si1 has a phosphorus content of less than 30 weight ppm.

According to another embodiment, the process for preparing alkylhalosilanes by reacting an alkyl halide, preferably $CH_3Cl$, with a solid material, termed contact material, formed of silicon powder and a catalytic system comprising at least one copper-based catalyst and promoter additives β1 and β2 in a fluidized bed reactor, is implemented as follows:

a) a first silicon Si1 is introduced, having an aluminum content of 0.12 to 0.18 weight %, a calcium content of less than 0.2 weight %, and a phosphorus content of less than 50 weight ppm, then b) a second silicon Si2 is introduced, alone or optionally in a mixture with Si1, having an aluminum content of 0.10 to 0.15 weight %, a calcium content of less than 0.2 weight %, and a phosphorus content of between 50 and 250 weight ppm, with the proviso that the aluminum content of the silicon Si2 is less than that of the silicon Si1.

Operating in this way allows a reduction in the average amount of aluminum employed in the process and thus makes it possible to limit the drawbacks associated with the accumulation of aluminum, as described above: the drop in activity and in the selectivity of the reaction, and the formation of carbon deposits.

The merit of the inventors is in having demonstrated that in order to be able to respond at the same time to the various technical constraints and to improve the profitability of the process for manufacturing alkylhalosilanes, in other words to maintain for as long as possible a high selectivity for dialkyldihalosilane and a high activity of the reaction while minimizing the deposits of carbon, it is necessary to combine the use of two well-defined grades of silicon, Si1 and Si2, in a specific order. This new process has the advantage of reducing the frequency of the technical halts to the process known in the prior art, where the material present in the reactor is discharged and the reactor is cleaned. This improvement allows the duration of industrial operations to be extended and allows a reduction in the frequency and duration of the reactor shutdowns during which the reactor is discharged, cleaned, then filled with silicon to start a new industrial operation. The spent material discharged is destroyed. Consequently, the greater the duration of the industrial operation, the higher the overall yield of silicon and the lower the ratio of tonnes of silicon destroyed per ton of silicon consumed.

According to one preferred embodiment, step (a) is operated as follows: the fluidized bed reactor is filled initially with the silicon Si1 as described above, and the reactor is fed continuously, employing:

step (a) then step (b) of the process according to the invention, or step (b) of the process according to the invention.

The feeding of Si2 into the reactor, which is step (b) of the process according to the invention, may commence as soon as the production of alkylhalosilanes starts, to replace the silicon consumed by the reaction, or after a period of feeding with Si1. Accordingly, the feeding of Si2 into the reactor may commence when the reaction material has been renewed at least once, in other words when the equivalent of the initial mass of silicon present in the reactor has been consumed. The duration of industrial operations is evaluated with the number of times the equivalent of the initial mass of silicon present in the fluidized bed reactor has been consumed (referred to as the number of reactor renewals). According to another embodiment, feeding with Si2 commences when the reactor renewal number is greater than 1.5.

For economic reasons, the silicon generally used for preparing alkylhalosilanes is metallurgical silicon, produced by carboreduction of silica in an electrical furnace, then refined in order to adjust the level of its main impurities, such as aluminum and calcium, and so to satisfy the specifications required by the market. It also contains secondary impurities, contributed by the raw materials, which the process of production and refining is not always able to remove. These impurities, and also the level at which they are present in the silicon, of in general between 10 and 500 mass ppm, are very heavily dependent on the origin of the raw materials used. The most common of these secondary impurities are phosphorus, sulfur, boron, carbon, or metals such as titanium, copper, magnesium, manganese, vanadium, nickel, zirconium, etc. In order to obtain the desired phosphorus content in the metallurgical silicon, various methods may be used. For example, patent EP 0272860 describes a method for regulating the amount of phosphorus in metallurgical silicon, by introducing phosphorus into the furnace via the raw materials such as the coal and charcoal used for the carboreduction, or via phosphorus compounds such as $Cu_3P$, FeP, CaP, etc. Patent EP 0273635 describes a method of manufacturing silicon to guarantee a phosphorus content of 25 to 2500 mass ppm, by addition of a nonvolatile compound of phosphorus after the casting of the silicon, before or after refining. Patent EP 1211223 describes the addition to the electric furnace of an SiP alloy, prepared beforehand, containing more than 75% silicon.

The effect of the amounts of impurities in the silicon (Al, Ca, P, Fe, etc.) on the process for preparing alkylhalosilanes has been widely studied, but the results of these studies are often contradictory, given the need also to take account of interactions between the various impurities, the catalysts and promoters used, and the granulometry of the silicon employed.

The amount of aluminum, calcium, and phosphorus in the various grades of silicon employed may be measured by various analytical techniques such as, for example, X-ray fluorescence, inductively coupled plasma atomic emission spectroscopy (ICP-AES), or atomic absorption spectroscopy.

Preferably, the second silicon Si2, introduced alone or optionally in a mixture with Si1, has an aluminum content of 0.11 to 0.15 weight %, a calcium content of less than 0.2 weight %, and a phosphorus content of between 50 and 200 weight ppm.

More preferably still, the second silicon Si2, introduced alone or optionally as a mixture with Si1, has an aluminum content of 0.1 to 0.15 weight %, a calcium content of less than 0.2 weight %, and a phosphorus content of between 50 and 150 weight ppm.

The use of a silicon Si2 having a phosphorus content of more than 50 weight ppm removes the need to add phosphorus in the form of promoter additive, thereby avoiding the problems typically encountered in the introduction and homogenization of the reaction mixture when adding the small amount of solid additive needed to give a concentration of 50 to 250 ppm in the fluidized bed. The process according to the invention, of course, does not rule out the addition of phosphorus as a promoter additive. It is important to control the granulometry of the silicon powder used in the process. Preferably, the silicon powder Si1 and/or Si2 introduced into the reactor has a particle size distribution such that 10 weight % of the particles have a diameter of less than 30 µm, 50 weight % of the particles have a diameter of less than 200 µm, and 90 weight % of the particles have a diameter of less than 400 µm.

More preferably, the silicon powder Si1 and/or Si2 introduced into the reactor has a particle size distribution such that 10 weight % of the particles have a diameter of less than 20 µm, 50 weight % of the particles have a diameter of less than 100 µm, and 90 weight % of the particles have a diameter of less than 300 µm.

More preferably still, the silicon powder Si1 and/or Si2 introduced into the reactor has a particle size distribution such that 10 weight % of the particles have a diameter of less than 5 µm, 50 weight % of the particles have a diameter of less than 60 µm, and 90 weight % of the particles have a diameter of less than 200 µm.

There are various known techniques by which the granulometry of the silicon powder can be measured, such as, for example, the screening of the silicon powder, followed by the weighing of the various fractions obtained, or by laser diffraction.

With regard to the catalytic system, the copper-based catalyst may be metallic copper, a copper-based alloy, or a copper-based compound, and/or mixtures thereof. As a copper compound, the following in particular may be used: a copper halide such as, for example, cuprous chloride or cupric chloride; a copper carboxylate such as, for example, cuprous formate, cupric formate, cuprous acetate, or cupric acetate; a copper oxide such as, for example, $Cu_2O$ or CuO and/or mixtures thereof. Cuprous chloride (CuCl) is an advantageous catalyst which may optionally be present in the form of beads as described in patent EP 1902060. The copper-based catalyst is used advantageously in an amount by weight of 1% to 10%, relative to the total weight of silicon employed.

According to one particular embodiment, the catalytic system further comprises a promoter additive β1 based on metallic zinc and/or on a compound of zinc, and a promoter additive β2 based on tin and/or on a compound of tin.

The promoter additive β1 used is preferably metallic zinc and/or zinc chloride. The promoter additive β1 is present in an amount by weight lying within the range from 0.01% to 2%, preferably from 0.01% to 0.5% (calculated in terms of zinc metal relative to the weight of silicon employed). Up to 90 weight % of the zinc, preferably up to 50 weight % of the zinc, may be replaced by another metal which catalyzes the chlorination of copper and/or which forms a low-melting-point phase or a eutectic with copper salts and/or alkali metal salts. Metals which may be suitable include cadmium, aluminum, manganese, nickel, and silver.

The amount by weight of tin and/or of tin compound (promoter additive β2, the amount of which is calculated by weight of tin metal) lies within the range from 10 to 500 ppm and, preferably, from 30 to 300 ppm, relative to the mass of silicon employed. It is necessary to have at least 10 ppm of tin metal. Moreover, an amount by weight of more than 500 ppm would have a detrimental effect on the reaction and in particular on the selectivity. The tin-based compound used is, for example, tin chloride. The promoter additive β2 which is used preferably is tin metal; advantageously, this metallic tin may be added in the form of bronze.

Other promoter additives may optionally be added, such as Cs, K, and Rb. It is possible to use halides, and for example the chloride, and carboxylates, and for example the formate or the acetate. Cesium chloride, potassium chloride, rubidium chloride and/or a mixture of these compounds are preferably used.

Phosphorus may also be used as a promoter additive. Its amount by weight (calculated as weight of elemental phosphorus relative to the mass of silicon employed) lies within the range from 50 to 1000 ppm and preferably of from to 500 ppm and more preferably still of from 80 to 300 ppm; below 50 ppm, the action of the phosphorus cannot really be detected, and above 1000 ppm the phosphorus has a poison effect. The phosphorus used as promoter additive may be elemental phosphorus, such as red phosphorus, white phosphorus, and black phosphorus, for example, or phosphorus-based compounds. Phosphorus-based compounds which may be used include metal phosphides and, for example, aluminum phosphide, calcium phosphide $Ca_3P_2$, copper phosphide $Cu_3P$, nickel phosphide $NiP_2$, tin phosphide SnP, iron phosphides FeP, $Fe_2P$, and $Fe_3P$, zinc phosphides $Zn_3P_2$ and $ZnP_2$, and silicon phosphide.

The copper-based catalyst and the various promoter additives are introduced into the reactor in the form of particles, and the average diameter of at least 50 weight % of the particles is advantageously between 1 and 200 µm.

The direct synthesis reaction takes place at a temperature lying within the range from 260 to 400° C. and, preferably, from 280 to 380° C., and more preferably from 285 to 330° C. It may be carried out, wholly or partly, under an absolute pressure of alkyl halide which is equal to atmospheric pressure (1 bar) or greater than atmospheric pressure; in the latter case, the reaction is operated generally under an absolute pressure of from 1.1 to 8 bar and preferably from 1.5 to 4 bar.

For the performance of the direct synthesis reaction, it is possible, as is well known, to carry out beforehand, advantageously, an initial step of activation of the contact material (formed by the silicon powder(s), the catalyst, and the promoter additives). One of the suitable means of activation may involve bringing the contact material to a certain temperature, which may be a few degrees to a few tens of degrees above or below the temperature selected for the direct synthesis reaction, and which is situated in the general range from 260 to 400° C., and preferably from 280 to 380° C., and more preferably from 285 to 330° C.

When the reaction is implemented, it is possible, by using the process according to the invention, in either an agitated bed or a fluidized bed, at a temperature of from 260° C. to 400° C. and preferably from 280 to 380° C., to obtain a high selectivity for dialkyldihalosilane, a low amount by weight of heavy by-products, and yet a highly satisfactory mean activity. These high performance levels can be maintained for a long time, and allow longer industrial operations with less regular, and shorter, phases of reactor shutdown for discharge and cleaning, these phases being shorter because of the reduced fouling of the reactor.

Other advantages and features of the present invention will become apparent from a reading of the examples below, which are given for the purpose of illustration but not in any way of limitation.

EXAMPLES

Tests were conducted in a laboratory agitated-bed pilot reactor in order to test different grades of silicon having variable aluminum, calcium, and phosphorus contents. The method of operating in all of the tests conducted in the laboratory is as follows: a vertical, cylindrical stainless reactor with an inside diameter of 85 mm and a height of 170 mm, equipped with a metallic stirrer and with a sparger made of sintered stainless steel, is charged with the following: 386 g of silicon, 14.7 g of CuCl, 0.095 g of Zn, and 0.46 g of bronze containing 10 weight % tin. The silicon is charged in the form of a powder in which at least 50 weight % of the particles have a diameter of less than 160 µm. The temperature of the reactor is regulated at 295° C., the pressure is maintained at 3.5 bar absolute, and the methyl chloride flow rate is set at 125 g/h throughout the test, which lasts for an average of 20 hours. The products of the reaction are collected and analyzed by gas chromatography. The selectivity is evaluated by the mean weight ratio MTCS/DMDCS and by the percentage of heavy products formed, relative to the total amount of silanes obtained.

The mean activity of the catalytic system is evaluated in terms of grams of silanes produced per hour per kg of silicon.

Table 1 below presents the results obtained with grades of silicon having variable aluminum and calcium contents.

TABLE 1

Silicon with variable aluminum and calcium contents

| Si grade | Al (wt %) | Ca (wt %) | Ratio MTCS/DMDCS | Yield of heavy products (wt %) | Mean activity (g silanes/ h/kg Si) |
|---|---|---|---|---|---|
| Si a | 0.178 | 0.084 | 0.04 | 6.2 | 227 |
| Si b | 0.142 | 0.08 | 0.04 | 8.1 | 180 |
| Si c | 0.073 | 0.038 | 0.06 | 4.9 | 106 |

For these three Si grades, the phosphorus content is between 20 and 25 weight ppm.

The results presented in table 1 show that when the aluminum content of the silicon is reduced, the mean activity of the reaction goes down sharply. Accordingly, if the aluminum content is reduced by 60%, the mean activity drops by 55% and the selectivity of the reaction is degraded (the ratio MTCS/DMDCS increases from 0.04 to 0.06, i.e., by 50%). Such substantial drops in the activity and the selectivity of the reaction are undesirable for an industrial process.

Table 2 below presents the results obtained with grades of silicon having variable aluminum and phosphorus contents.

TABLE 2

Silicon with low aluminum content and high P content

| Si grade | Al (wt %) | Ca (wt %) | P (wt ppm) | Ratio MTCS/ DMDCS | Yield of heavy products (wt %) | Mean activity (g silanes/ h/kg Si) |
|---|---|---|---|---|---|---|
| Si d | 0.135 | 0.088 | 20 | 0.05 | 5.1 | 171 |
| Si e | 0.116 | 0.088 | 150 | 0.03 | 3.8 | 179 |

The examples in table 2 show that despite a decrease by 15% in the aluminum content of the silicon, the presence of 150 ppm of phosphorus in the silicon enhances the activity and the selectivity of the reaction. The activity of the reaction has increased by 5%, the ratio MTCS/DMDCS decreases by 40%, and the yield of heavy products decreases by 25%.

This grade of silicon (corresponding to silicon e) therefore has the advantage of containing less aluminum but without resulting in a deterioration in the selectivity or activity of the reaction.

Industrial Tests

Industrial tests were carried out in order to validate the results obtained in the laboratory, with two different grades of silicon, which are described in table 3 below.

TABLE 3

Grades of silicon used for the industrial tests

| Silicon grade | Al (wt %) | Ca (wt %) | P (wt ppm) | Fe (wt %) |
|---|---|---|---|---|
| Si X | 0.16 | 0.08 | 25 | 0.4 |
| Si Y | 0.12 | 0.07 | 114 | 0.4 |

Profile of the Industrial Operations:

The fluidized bed reactor is charged with silicon, CuCl, and promoters based on zinc and tin. The reactor is fed with methyl chloride continuously and is maintained at a temperature of between 295 and 300° C. Silicon is also fed continuously to replace that consumed by the reaction forming methylchlorosilanes. The catalysts and promoters are also fed continuously or semicontinuously in order to maintain their concentration constant in the reaction material. The duration of the industrial operations is evaluated by the number of times the initial mass of silicon has been completed renewed in the reactor (referred to as number of renewals of the reactor).

We carried out three types of industrial operations.

OP1 (comparative process), where only Si X was supplied throughout the operation. Three operations were carried out, with similar results. The results are presented in averaged form.

OP2 (process according to the invention), in which the initial charge of silicon was made with Si X, then the reactor was first fed with Si X, and, when the number of renewals of the material in the reactor reached 1.5, the reactor was fed with Si Y until the end of the operation. Two operations were conducted: OP2a and OP2b.

OP3 (comparative process), in which only Si Y was supplied throughout the operation.

The only difference in the conduct of these operations is the grade of silicon used for continuous supply to the fluidized bed reactor. The granulometry of the two grades of silicon used is comparable, since they were ground and screened in the same industrial installation. The temperature, the pressure, and the concentrations of catalyst (CuCl) and promoters (Zn and Sn) are identical. Generally speaking, the granulometry of the silicons X and Y used is such that at least 50 wt % of the silicon particles have a diameter of less than 200 µm.

Table 4 below shows the duration of each of these industrial operations and the state of fouling of the reactor, owing to deposits of carbon, at the end of operation.

TABLE 4

| Type of industrial operation | Duration of OP (number of renewals of the reactor) | Reactor fouling (carbon deposits) |
|---|---|---|
| OP1 (comparative) | 24 | Reactor fouled |
| OP2a (inventive) | 28 | Clean - no fouling |
| OP2b (inventive) | 32 | Clean - no fouling |
| OP3 (comparative) | 1 | Reactor clean |

Accordingly, in the OP2 industrial operations (process according to the invention), a prolongation is obtained in the duration of the operation, relative to an OP1 operation (comparative process). The number of renewals of the reactor increases from 24 to 28, or a 16% increase in the industrial duration of the operation for OP2a, and from 24 to 32 for OP2b, or a 33% increase in the industrial duration of the operation.

On the other hand, in industrial operation OP3 (comparative process), the reaction material has too low a reactivity at the start of the reaction, and the reaction did not reach the required productivity. The operation had to be halted rapidly after a single reactor renewal; this is not industrially viable. The Si Y grade cannot be used from the start of the industrial operation.

Moreover, the industrial operations of type OP2 (process according to the invention) resulted in a clean reactor, without fouling; this facilitates the operations of cleaning and readying of the installations.

Table 5 below shows the change in the selectivity and activity of the reaction as a function of the progress of the reaction for the operations OP1 and OP2a.

TABLE 5

| Duration of OP (number of renewals of the reactor) | Ratio MTCS/DMDCS | | Yield of heavy products (wt %) | |
|---|---|---|---|---|
| | OP1 comparative | OP2a inventive | OP1 comparative | OP2a inventive |
| 2 | 0.082 | 0.055 | 4.9 | 2.9 |
| 4 | 0.075 | 0.057 | 5.8 | 5.9 |
| 8 | 0.077 | 0.069 | 6.0 | 4.6 |
| 12 | 0.085 | 0.076 | 6.6 | 5.6 |
| 16 | 0.115 | 0.073 | 7.8 | 5.8 |
| 20 | 0.121 | 0.079 | 6.2 | 7.1 |
| 24 | 0.158 | 0.075 | 6.7 | 5.5 |
| 28 | | 0.085 | | 7.1 |

Accordingly, it is found for operation OP2a (process according to the invention) that a high selectivity (ratio MTCS/DMDCS ≤0.100) is maintained throughout the operation, whereas for the industrial operation OP1 (comparative process), the selectivity deteriorates substantially after 16 renewals of the reactor (ratio MTCS/DMDCS >0.100).

In order to evaluate the activity of the reactor, in other words its hourly productivity, table 6 below shows the change in activity as a function of the operating time (always measured by the reactor renewal number). This activity was initially measured in grams of methylchlorosilanes produced per hour per kg of silicon. The value of 100 was attributed for all of the operations at the initial value (measured at ten reactor renewals), and table 6 below presents the percentage change relative to this initial value.

TABLE 6

| OP duration | Normalized activity | | |
|---|---|---|---|
| (number of reactor renewals | OP1 comparative | OP2a inventive | OP2b inventive |
| 2 | 100 | 100 | 100 |
| 4 | +4% | +11% | +6% |
| 8 | +12% | 0 | +18% |
| 12 | +14% | +1% | +17% |
| 16 | +11% | −4% | +9% |
| 20 | +2% | +3% | +16% |
| 24 | −16% | −4% | +13% |
| 28 | | −12% | +11% |
| 32 | | | −6% |

These results show that during OP2 operations (process according to the invention), success is achieved in maintaining the initial level of activity for a greater number of reactor renewals, thereby opening up the possibility of longer operating times than for the process OP1 (comparative process), where the activity fell by 16% after 24 reactor renewals.

Lastly, table 7 below shows the accumulation of aluminum in the reaction material during OP1 and OP2 operations. To determine the aluminum content of the reaction material, a sample is taken from the reactor and is analyzed by X-ray fluorescence.

TABLE 7

| OP duration | Accumulation of Al (wt ppm) | | |
|---|---|---|---|
| (number of reactor renewals | OP1 comparative | OP2a inventive | OP2b inventive |
| 2 | 1797 | 1720 | 1550 |
| 4 | 2680 | 2760 | 1920 |
| 8 | 4260 | 2900 | 2680 |
| 12 | 5500 | 3640 | 3200 |
| 16 | 6280 | 3960 | 3900 |
| 20 | 7630 | 4000 | 4400 |
| 24 | 8607 | 4910 | 5130 |
| 28 | | 5700 | 5730 |
| 32 | | | 7000 |

The increase in the aluminum content of the reaction material is slower for the OP2 industrial operations (process according to the invention). After 24 reactor renewals, the reaction materials in the OP2a and OP2b operations show a much lower aluminum content (approximately −35%) than the reaction material in operation OP1 (comparative process). This result should be linked with the final fouling rate of the reactor that is observed for each industrial operation (table 4).

These examples illustrate well the objective of this invention. By using the process for direct synthesis of alkylhalosilanes in accordance with the invention, a high selectivity for dialkyldihalosilane, a low weight content of heavy by-products, and a highly satisfactory mean activity are obtained. These good performance levels can be maintained for longer and allow longer industrial operations with less frequent and shorter phases of reactor shutdown for discharge and cleaning, since the fouling of the reactor is reduced and its cleaning is easier.

The invention claimed is:

1. A process for preparing alkylhalosilanes, the process comprising reacting an alkyl halide with a solid material, termed contact material, formed of silicon powder and a catalytic system comprising at least one copper-based catalyst and promoter additives β1 and β2 in a fluidized bed reactor, wherein the process further comprises:
   a) introducing a first silicon Si1, having an aluminum content of 0.10 to 0.18 weight %, a calcium content of less than 0.2 weight %, and a phosphorus content of less than 50 weight ppm, and then
   b) introducing a second silicon Si2, alone or optionally in a mixture with Si1, having an aluminum content of 0.10 to 0.15 weight %, a calcium content of less than 0.2 weight %, and a phosphorus content of between 50 and 250 weight ppm.

2. The process as claimed in claim 1 the process wherein:
   a) the first silicon Si1 has an aluminum content of 0.12 to 0.18 weight %, a calcium content of less than 0.2 weight %, and a phosphorus content of less than 50 weight ppm, and
   b) the second silicon Si2, alone or optionally in a mixture with the Si1, has an aluminum content of 0.10 to 0.15 weight %, a calcium content of less than 0.2 weight %, and a phosphorus content of between 50 and 250 weight ppm, with the proviso that the aluminum content of the silicon Si2 is less than that of the silicon Si1.

3. The process as claimed in claim 1, wherein the second silicon Si2, introduced alone or optionally in a mixture with the Si1, has an aluminum content of 0.11 to 0.15 weight %, a calcium content of less than 0.2 weight %, and a phosphorus content of between 50 and 200 weight ppm.

4. The process as claimed in claim 1, wherein the silicon powder Si1 and/or Si2 introduced into the reactor has a particle size distribution such that 10 weight % of the particles have a diameter of less than 30 μm, 50 weight % of the particles have a diameter of less than 200 μm, and 90 weight % of the particles have a diameter of less than 400 μm.

5. The process as claimed in claim 1, wherein the silicon powder Si1 and/or Si2 introduced into the reactor has a particle size distribution such that 10 weight % of the particles have a diameter of less than 20 μm, 50 weight % of the particles have a diameter of less than 100 μm, and 90 weight % of the particles have a diameter of less than 300 μm.

6. The process as claimed in claim 1, wherein the silicon powder Si1 and/or Si2 introduced into the reactor has a particle size distribution such that 10 weight % of the particles have a diameter of less than 5 μm, 50 weight % of the particles have a diameter of less than 60 μm, and 90 weight % of the particles have a diameter of less than 200 μm.

7. The process as claimed in claim 1, wherein the copper-based catalyst is selected from the group consisting of metallic copper, a copper-based alloy, a copper-based compound, and mixtures thereof.

8. The process as claimed in claim 1, wherein the copper-based catalyst is selected from the group consisting of metallic copper, a copper-based alloy, a copper halide, a copper carboxylate, a copper oxide, and mixtures thereof.

9. The process as claimed in claim 1, wherein the copper-based catalyst is used in an amount by weight of 1% to 10% relative to the total weight of silicon employed.

10. The process as claimed in claim 1, wherein the additive β1 is metallic zinc and/or zinc chloride.

11. The process as claimed in claim 1, wherein the additive β2 is tin metal.

12. The process as claimed in claim 1, wherein the direct synthesis reaction is carried out at a temperature lying within the range from 260° C. to 400° C.

13. The process as claimed in claim 1, wherein the alkyl halide is $CH_3Cl$.

* * * * *